United States Patent
Nielsen et al.

(10) Patent No.: US 6,881,759 B2
(45) Date of Patent: Apr. 19, 2005

(54) PROCESS FOR THE PREPARATION OF METHANOL

(75) Inventors: Poul Erik Højlund Nielsen, Fredensborg (DK); Cecilia Jaksland, Espergærde (DK); Jens Perregaard, Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 10/806,443

(22) Filed: Mar. 23, 2004

(65) Prior Publication Data

US 2004/0198847 A1 Oct. 7, 2004

(30) Foreign Application Priority Data

Apr. 7, 2003 (DK) .................................. PA 2003 00529

(51) Int. Cl.[7] .............................................. C07C 27/00
(52) U.S. Cl. ..................... 518/705; 700/711; 700/712
(58) Field of Search ................ 518/700, 705, 518/711, 712

(56) References Cited

U.S. PATENT DOCUMENTS

| | | |
|---|---|---|
| 1,302,011 A | 4/1919 | Christensen |
| 4,628,066 A | 12/1986 | Bonnell et al. |
| 4,766,154 A | 8/1988 | Bonnell et al. |
| 4,910,277 A | 3/1990 | Bambury et al. |
| 5,179,129 A | 1/1993 | Studer |
| 5,284,878 A | 2/1994 | Studer et al. |
| 5,364,887 A * | 11/1994 | Konig et al. ................ 518/713 |
| 5,384,335 A | 1/1995 | Tierney et al. |
| 5,520,890 A | 5/1996 | Lorentzen et al. |

FOREIGN PATENT DOCUMENTS

JP        57126434        8/1982

* cited by examiner

*Primary Examiner*—J. Parsa
(74) *Attorney, Agent, or Firm*—Dickstein Shapiro Morin & Oshinsky LLP

(57) ABSTRACT

The present invention is a novel process for methanol production in a liquid phase reactor from a synthesis gas comprising of hydrogen, carbon dioxide and carbon monoxide. The liquid phase reactor contains a solid catalyst suspended in methanol. In this innovation, methanol acts both as a product and as a suspension medium for the catalyst. The new innovation exploits the condensing conditions for methanol production. By operating at condensing conditions, the methanol partial pressure at equilibrium is higher than the boiling pressure of methanol at the given temperature. Hence the produced methanol of the equilibrium composition condenses creating the potential of more gas to be converted. Since equilibrium is not a limiting factor, high conversions can be obtained.

12 Claims, 1 Drawing Sheet

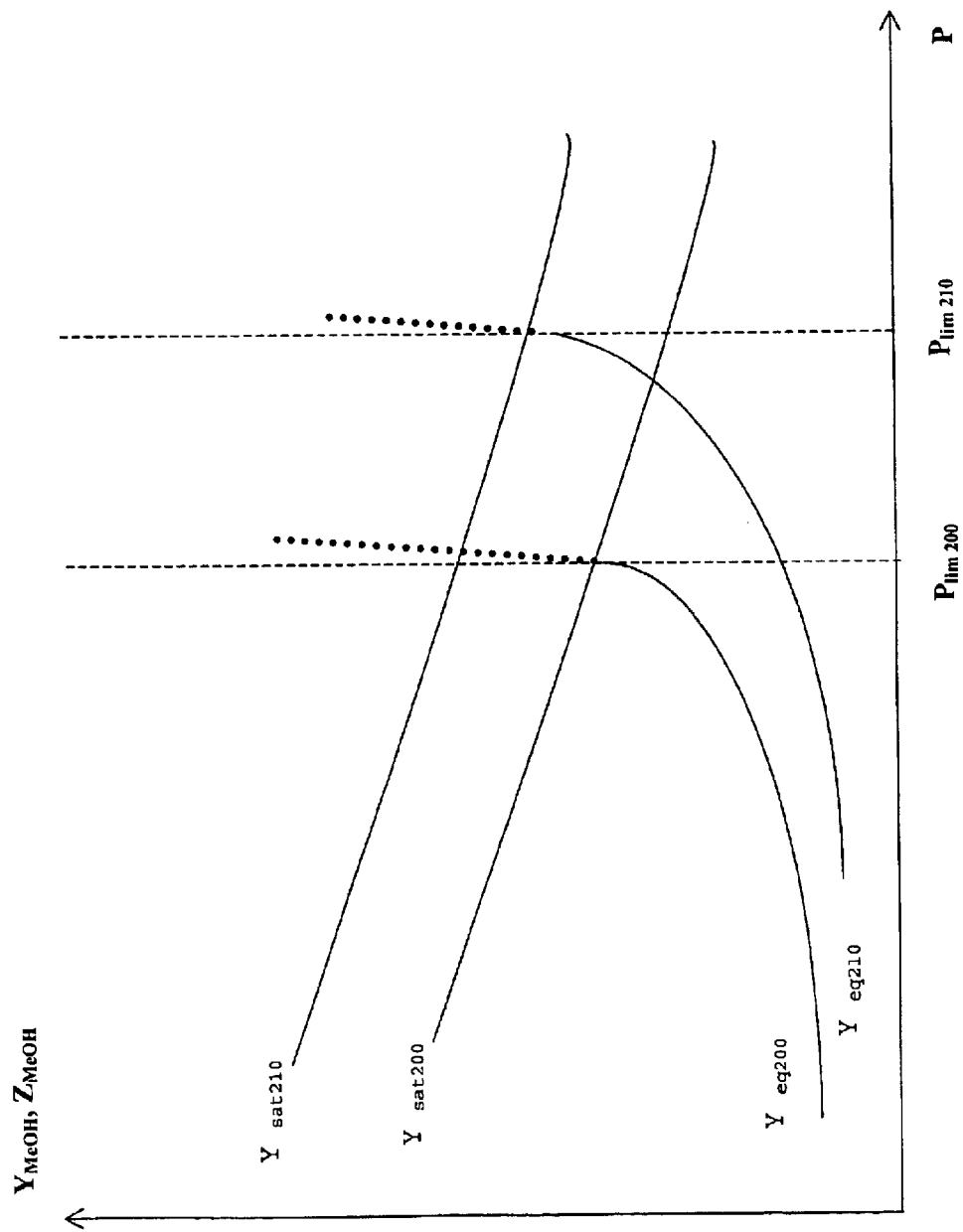
FIGURE

PROCESS FOR THE PREPARATION OF METHANOL

The present invention relates to conversion of synthesis gas into methanol at condensing conditions. In particular, the invention is a methanol preparation process being carried out in a slurry reactor, wherein condensed methanol product is utilised as suspension medium for a catalyst being active in the methanol synthesis reactions.

Synthesis gas is any gas composition comprising hydrogen and carbon dioxide and/or carbon monoxide being able to establish condensing conditions.

BACKGROUND OF INVENTION

Heterogeneous methanol synthesis is in today's practice carried out by reacting carbon oxides with hydrogen in the presence of copper-based catalysts according to the following equations:

$$3H_2 + CO_2 = CH_3OH + H_2O \quad (1)$$

$$2H_2 + CO = CH_3OH \quad (2)$$

The methanol synthesis catalyst also catalyses the Water Gas Shift (WGS) reaction, $$CO + H_2O = CO_2 + H_2 \quad (3)$$

and the Reverse Water Gas Shift (RWGS) reaction, $$CO_2 + H_2 = CO + H_2O \quad (4)$$

In large-scale methanol plants, the gas phase synthesis reactor is typically a cooled tubular reactor or a multistage adiabatic reactor. The typical temperature range for methanol synthesis is 200–300° C. Cooled reactors normally operate at approximately 250° C., whereas adiabatic reactors typically operate between 220° C. and 300° C. The reaction to methanol is strongly exothermic, and efficient heat removal is a problem. This limits the range of composition of the feed gas that can be treated in a tubular reactor, for example CO rich gases are very exothermic and difficult to process. Inefficient heat removal leads to hot zones in the reactor, and the catalyst may thus deactivate faster. A serious problem is by-product formation being promoted at high temperatures appearing particularly in the hot zones. For example the production of ethanol, and methyl formate increases at increasing temperatures. Alcohols, esters and ketones are difficult to separate from methanol-water mixtures being withdrawn from the process due to the formation of azeotropes.

With respect to pressure, the typical operating pressure in methanol synthesis is within 50–100 bar. Cooled reactors operate at a pressure of around 50 bar, whereas adiabatic reactors generally operate at a higher pressure, typically around 80 bar.

The synthesis gas used in methanol synthesis can be derived from natural gas either by steam reforming of natural gas or by autothermal reforming.

The conversion rate to methanol is determined by the thermodynamic equilibrium constant, which typically results in process effluent concentrations being in the range between 4% and 10% in all cases with only a partial conversion of the carbon oxides. Thus, to obtain maximum use of the produced synthesis gas, a recycle of the unconverted gas is necessary. A high recycle ratio ensures high conversion. A high recycle flow through the reactor increases the compression cost. Before recycling, the effluent gas is cooled and separated from the liquid product. The effluent gas can be enriched in hydrogen by employing, for example, membrane separation. The enriched gas is recycled to the methanol reactor. The inert level, in particular methane is kept under control by purge.

Beside of the above mentioned tubular methanol reactor being conventionally employed in the industrial production of methanol use of slurry bed methanol reactors have also been suggested in the literature.

The original invention of the slurry reactor was made by Chem Systems and is described in U.S. Pat. No. 3,888,896. Herein a preparation process is described using an inert organic liquid such as pseudocumene as the slurry medium.

A series of patents from Air Products (U.S. Pat. Nos. 4,628,066, 4,766,154, 4,910,277, 5,179,129 and 5,284,878) describe the application of a slurry reactor for methanol synthesis. These applications are characterised by the suspension of the methanol catalyst in an inert liquid, typically a high-molecular-weight hydrocarbon. Only partial conversion of methanol is considered here, as the reaction conditions are given as 30–100 bar and 210–250° C.

The finely divided catalyst must be separated from the liquid product. U.S. Pat. No. 5,520,890 by Den Norske Stats Oljeselskap A. S. describes an apparatus for solid-liquid slurry treatment. The process described in this patent provides a solution for the separation of fine catalyst particles from the liquid by operation in tubes including filtrate zones.

JP Patent No. 57126434 discloses a methanol preparation method from CO and/or $CO_2$ in the presence of a water-soluble basic substance where water is used as slurry medium.

A completely different approach to methanol synthesis from alkyl formates was first described by J. A. Christiansen in U.S. Pat. No. 1,302,011. This approach is also described in U.S. Pat. No. 5,384,335 and consists of two distinct steps:

First Step:

Carbonylation of methanol to methyl formate, $HCOOCH_3$ ($=C_2H_4O_2$), in a basic medium e.g.

$$CH_3OH + CO = C_2H_4O_2 \quad (5)$$

Second Step:

Reduction of methyl formate to methanol on a Cu-based catalyst $$C_2H_4O_2 + 2H_2 = 2CH_3OH \quad (6)$$

Various solvents are described including the use of methanol as a solvent. The conditions under which the above reactions take place differ significantly from the conditions applied in industrial methanol synthesis. Reaction 5 requires a temperature much lower than 200° C., whereas reaction 6 is preferably carried out at much higher temperatures. In some processes the reactions are actually carried out in separate reaction vessels.

The most important difference between the above process and the industrial methanol synthesis is the role of $CO_2$. In the above process $CO_2$ acts as a poison for reaction 5, whereas in the heterogeneous synthesis of methanol (reaction 1) $CO_2$ is a necessary reactant. $H_2O$ also acts as a poison in the above process.

A conversion not limited by the thermodynamic equilibrium can be obtained in the case of a methanol product removal under synthesis. U.S. Pat. No. 5,262,443 to Haldor Topsoe A/S describes such a process where methanol synthesis is carried out under condensing conditions in a fixed bed in a cooled tubular reactor. Methanol condensing conditions include a temperature below the critical temperature of methanol, i.e. 240° C. In addition, the methanol partial pressure calculated from the gas phase equilibrium constant is larger than the boiling pressure of methanol at the actual temperature. The process is most conveniently carried out with a stoichiometric synthesis gas being enriched in CO.

The removal of heat in the tubular reactor disclosed in the later patent and in tubular methanol reactors in general is one of the key problems of such a process. The most serious problem when employing fixed catalyst bed methanol reactors is formation of by-products being formed in hot zones of the bed caused by the highly exothermic nature of the methanol reactions in the catalyst bed.

In contrast to the above discussed prior art, the present invention is a preparation method for methanol at condensing reaction conditions wherein the methanol catalyst is suspended in methanol and water, and wherein the product being formed on the suspended catalyst (primarily methanol and water) continuously condenses and being absorbed in the suspension and thus makes up the suspension medium for the methanol catalyst.

When carrying out the methanol reactions in a catalyst suspension heat being produced during the reactions is effectively controlled. Formation of hot spots or hot zones a known problem in the fixed bed reactors is prevented since heat is transferred and distributed uniformly within the liquid. The efficient temperature control is necessary to reduce by-product formation as mentioned above and to minimise deactivation of the catalyst.

SUMMARY OF THE INVENTION

The present innovation is a liquid phase process for the production of methanol being carried out in a slurry-bed reactor. In this process, methanol product is utilised as a catalyst suspension liquid medium. This process exploits the condensing conditions to produce methanol. The methanol partial pressure (calculated from the gas phase equilibrium constant) is larger than the boiling pressure of methanol at the given temperature resulting in a condensation of the methanol product. Synthesis gas conversion is thereby not limited by equilibrium. The equilibrium and saturation composition is affected by temperature. For an increase in temperature, the pressure needs to be increased to obtain condensing conditions.

Accordingly, the invention is in its broadest aspect a process for preparing methanol from a synthesis gas comprising carbon monoxide, carbon dioxide and hydrogen by steps of:

(a) passing the synthesis gas into a reactor containing a solid methanol conversion catalyst suspended in a liquid phase of methanol and water;

(b) reacting the synthesis gas in presence of the suspended catalyst at a pressure and temperature, where methanol being formed on the catalyst condenses into the liquid phase; and (c) withdrawing from the reactor a part of the liquid phase containing formed methanol product.

BRIEF DESCRIPTION OF DRAWING

Condensing conditions are defined as the operating conditions of a methanol synthesis, wherein the methanol saturation pressure is reached before the reaction equilibrium of the synthesis gas composition is reached. The critical temperature for methanol is 240° C. Non-condensing and condensing conditions are separated for a given synthesis gas composition at a given operating temperature by a pressure, $P_{lim}$. Above this pressure, condensing conditions are present whereas below this pressure, non-condensing conditions are present (see FIG.).

As the methanol saturation pressure increases with temperature and the equilibrium methanol pressure decreases with temperature, $P_{lim}$ increases with temperature. Above the saturation curve, the total mole fraction of methanol in the equilibrium mixture is depicted as a dashed line.

The characteristic of a preferred synthesis gas composition is a low $P_{lim}$. The typical condensing conditions for preferred synthesis gas compositions is at temperatures 190–240° C. and at pressures 60–140 bar.

In one embodiment of the present invention, the synthesis gas is compressed to a pressure higher than $P_{lim,t}$ and fed to the slurry methanol reactor operated at a temperature, t; the synthesis gas is converted in contact with a catalyst active in methanol synthesis to a degree, where condensing conditions are obtained resulting in a directly condensed methanol product and an effluent synthesis gas saturated with methanol; the directly condensed methanol product (primarily methanol, water and $CO_2$) constitutes the suspension liquid medium for the catalyst active in methanol synthesis; the effluent synthesis gas stream rich in methanol is cooled down and separated to attain further product retrieval. The directly condensed methanol product used as suspension liquid is conventionally separated and recovered from the solid catalyst particles e.g. by filtration. The solid catalyst particles are recycled to the slurry reactor. The resulting methanol product is obtained from both the directly condensed methanol product and the retrieved methanol from the effluent synthesis gas.

In the known liquid phase methanol processes, the liquid suspension medium is an inert hydrocarbon liquid and an additional liquid phase is introduced into the system. This additional liquid phase must be separated from the product methanol. By the inventive methanol process, there is no need for a liquid phase separation stage, since the product and suspension liquid is the same component, i.e. methanol and minor amounts of water. Hence, a high purity methanol product will be withdrawn from the reaction, and contamination of high molecular weight hydrocarbons can be avoided.

The liquid phase slurry reactor represents a solution to the heat removal problem in the known methanol process. The reactions for methanol formation from carbon monoxide and/or carbon dioxide are strongly exothermic. In gas phase reactors, the strong exothermic reaction creates a zone with high temperature of typical around 280° C. or higher within the catalyst tube, which promotes formation of by-products. The by-products formed are mainly higher alcohols such as ethanol, propanol, butanol, various esters and ketones. It is costly to separate these components from the methanol product due to the formation of azeotropes between ketones, esters and methanol and ethanol and water. As a further disadvantage, the catalysts within the hot zones deactivate more rapidly. In the liquid phase reactor, the liquid phase reaction heat is absorbed in the liquid. The temperature can be better controlled and no hot zones are formed. Hence the formation of by-products is kept at a minimum.

Since heat removal is more efficient in the liquid phase process, mixtures of a wide range of gas compositions can be treated. The main advantage of the invention is that a CO-rich synthesis gas can be treated. Synthesis gas mixture compositions in the range of 15–30 vol. % CO, 60–74 vol. % hydrogen and 0.5–15 vol. % carbon dioxide have been treated. For a low content of carbon dioxide, the concentration of water in the methanol product will be low.

The process of the invention has the advantage of providing a high single-pass conversion. The high conversion is obtained because the conversion of methanol is not limited by thermodynamic equilibrium at condensing conditions as mentioned above.

By the process according to the invention a synthesis gas containing carbon dioxide can be processed. This is advantageous because it is expensive to produce a synthesis gas with low $CO_2$.

Cooling of the process can be performed by using cooling tubes producing medium or low-pressure steam. The tubes can be arranged in the methanol/water slurry and ensure that the temperature is kept at an almost constant level. Circulation of liquid around the tubes provides an improved temperature distribution and control. In a tubular fixed-bed reactor, hot zones are usually formed in the centre of the catalyst tube since the reaction is very exothermic. This promotes by-product formation as already discussed above.

Even an effective temperature control does, however, not prevent formation of some small amounts of by-products, including the aforementioned higher alcohols, ketones and ester compounds.

A main advantage of the process according to the invention is that by-products being formed during the methanol reaction may be recycled to the reactor and the reaction suspension, which by means of the chemical equilibrium between methanol and by-products being formed by reaction of methanol with reactants being present in the suspension prevents net production of by-products as discussed in more detail below.

The produced raw methanol can be used either as fuel methanol or fractionated into chemical grade methanol.

DETAILED DESCRIPTION OF THE INVENTION

By the invention methanol synthesis gas into a liquid phase, which consists of catalyst suspended in methanol, thereby reacting the synthesis gas to produce methanol. A small fraction of water can be tolerated (0–3 vol. %) in the methanol suspension without a significant deactivation of the catalyst.

The process can be operated as a once-through process and as a process in which unconverted gas is recycled.

The separation of the methanol product from the catalyst may be accomplished by inserting filters within the reactor. This will prevent the catalyst from leaving the reactor. Other systems would include filtration of the product or cyclone treatment outside the reactor.

The synthesis gas is low in carbon dioxide giving a product with low water content. Results have shown that the water production is around 0.02 g/g methanol.

The low water content confirms that the water gas shift reaction is active and that most of the produced water is consumed by this reaction.

The results also show that water can be tolerated in the present catalyst system. A water concentration of 0.55 wt % does not decrease the reaction rate to a high extent.

The methanol product after reaction at for example 202° C. and 116 bar in a once-through process consists of small amounts of water (1.64 wt %), DME (0.19 wt %), methyl formate (0.92 wt %), ethanol (0.29 wt %), acetic acid methyl ester (0.09 wt %) and carbonic acid di-methyl ester (0.06 wt %). In addition, traces of acetone, methane dimethoxy, 1-propanol, formic acid(2-methyl ethyl ester) and carbonic acid dimethyl ester may be found (<0.03 wt %).

The present innovation provides means for keeping by-product concentration such as methyl formate concentration at a constant level in the reactor. Methyl formate can be separated from the methanol product and recycled to the reactor. By recycling a methyl-formate-rich stream to the reactor, chemical equilibrium will be established in the reactor and there will be no net production of methyl formate. Example 7 illustrates the reduction of methyl formate in the liquid phase from 35 mol % to 5 mol % at 200° C. and 132 bar. At these conditions reactions (10) and (11) are shifted towards methanol production

$$CH_3OH+CO=HCOOCH_3 \quad (7)$$

$$HCOOCH_3+2H_2=2CH_3OH \quad (8)$$

In this case an activated commercial catalyst available from Haldor Topsoe A/S under the tradename MK-101P is used for methanol production. This is a Cu/Zn/Al-based catalyst. A number of other catalysts for methanol production may also be employed.

EXAMPLES

The following examples illustrate the results obtained with a batch process system. The composition of the gases that have been treated is given in Table 1.

TABLE 1

| | Synthesis gas composition | | | |
|---|---|---|---|---|
| | Gas A [vol. %] | Gas B [vol. %] | Gas C [vol. %] | Gas D [vol. %] |
| $H_2$ | 60. | 74. | 60. | 60. |
| CO | 30. | 25.5 | 25. | 15. |
| $CO_2$ | 5. | 0.5 | 5. | 15. |
| $N_2$ | 5. | 0. | 10. | 10. |
| Total | 100.0 | 100. | 100. | 100. |
| $H_2$/CO | 2.0 | 3.0 | 2.4 | 4. |
| $CO_2$/CO | 0.17 | 0.02 | 0.2 | 1. |

Example 1

A 120 ml autoclave reactor was loaded with active catalyst and methanol. Activated MK-101 (pulverised) is employed as catalyst. The autoclave was connected to a gas reservoir that contained a mixture of synthesis gas "A" comprising of hydrogen (60 vol. %), nitrogen (5 vol. %), carbon monoxide (30 vol. %) and carbon dioxide (5 vol. %) at 21° C. and 162 bar. The volume of the gas reservoir was 0.5 l. The process was a closed batch system since neither gas nor liquid was removed from the system until the reaction was completed. The connection between the reactor and gas reservoir was opened. The reaction occurred in the autoclave at a constant pressure of 116 bar and a constant temperature of 202° C. The autoclave was agitated by stirring at 500 rpm. As the reaction proceeded, carbon dioxide and hydrogen were converted to methanol and water. The produced methanol and water condensed to liquid. Carbon monoxide reacted with water to produce hydrogen and carbon dioxide in the water gas shift reaction. The reactants were taken from the gas reservoir. The pressure drop in the gas reservoir was monitored and was used to determine the amount of gas consumed and hence the amount of methanol formed. With the pressure drop, the amount of methanol produced was calculated, assuming that reaction (7) resulted in the pressure drop. As the pressure in the gas reservoir had dropped to 121 bar, it was refilled to 162 bar and the reaction proceeded spontaneously until the gas reservoir pressure had dropped to 120 bar. Since the gas composition in the reactor changed with time, the reaction rate slowly decreased with time. A pressure drop corresponding to a gas consumption of 1.7 moles of synthesis gas resulted in 13.4 g of measured methanol product.

Table 2 illustrates the produced amount of methanol obtained for selected operating temperatures and pressures in the presented examples.

Example 2

Example 1 was repeated at a pressure of 109 bar and a temperature of 180° C., but with synthesis gas mixture "B" comprising of 74 vol. % hydrogen, 25.5 vol. % carbon monoxide and 0.5 vol. % carbon dioxide. A fresh catalyst suspension Pwas employed with activated catalyst. The gas was taken from the gas reservoir at 21.2° C. and a pressure of 168.9 bar. Agitation was maintained at 500 rpm. Reaction continued spontaneously until a gas reservoir pressure of 130.6 bar. 6.3 g of methanol product was produced.

Example 3

Example 1 was repeated, at a pressure of 137 bar and a temperature of 200° C. with the synthesis gas B from Example 2. The methanol suspension consisted of around 0.8 wt % of water originating from previous experiment. The same catalyst suspension was employed as in Example 2. The gas was taken from the reservoir at 170.4 bar at 21.6° C. The agitation rate was 500 rpm. At a reactor pressure of 131.4 bar, the reaction was terminated. The calculated product was 6.3 g.

TABLE 2

Conditions for methanol production

| Gas | Pressure (bar) | Temperature (° C.) | ΔP (bar) | MeOH (g) |
|---|---|---|---|---|
| A | 116 | 202 | 83.0 | 13.4 |
| B | 109 | 180 | 38.3 | 6.3 |
| B | 137 | 200 | 38.9 | 6.3 |
| C | 137 | 210 | 47.6 | 7.8 |
| D | 109 | 180 | 40.0 | 6.8 |

Example 4

Example 1 was repeated, but at a pressure of 137 bar and a temperature of 210° C. with synthesis gas mixture "C" comprising of 60 vol. % hydrogen, 10 vol. % nitrogen, 25 vol. % carbon monoxide and 5 vol. % carbon dioxide. The same suspension had been used for 5 previous experiments. The gas was taken from the gas reservoir at 21.2° C. and a pressure of 168 bar. Agitation was maintained at 500 rpm. The gas reservoir pressure dropped to 138.4 bar and the reservoir was refilled to 167 bar. Reaction continued spontaneously to a gas reservoir pressure of 149 bar. 7.8 g of methanol product was produced.

Example 5

Example 1 was repeated, but at a pressure of 109 bar and a temperature of 180° C. with synthesis gas mixture "D" comprising of 60 vol. % hydrogen, 10 vol. % nitrogen, 15 vol. % carbon monoxide and 15 vol. % carbon dioxide. The catalyst suspension had been used in previous experiments. The gas was taken from the gas reservoir at 21.3° C. and a pressure of 162 bar. Agitation was maintained at 500 rpm. Reaction continued spontaneously until a reservoir pressure of 122 bar. 6.8 g of methanol was produced.

Example 6

Influence of Water Concentration.

The influence of water concentration was investigated. The results are listed in Table 3.

(6a) Methanol Solution of <0.05 wt % Water

Fresh activated catalyst was employed in a methanol suspension of below 0.05 wt % water. The synthesis gas B was added at the operating conditions of 138 bar and 200° C. The gas was taken from the gas reservoir at 19.5° C. and a pressure of 167 bar. The pressure dropped to 137 bar in the reservoir. The reservoir was refilled twice to 166 bar. The pressure drop was 30.2, 21.4 and 4 bar, respectively, in each period. 9.1 g of methanol was produced. The water concentration in methanol after the experiment was 0.48 wt %.

(6b) Methanol Solution of 5 wt % Water

Example 6a was repeated but at 139 bar and 200° C. re-using the same catalyst as used in Example 6a. Water was added to an initial concentration of 5 wt % in methanol. The pressure drop was in total 48.3 bar, and 7.9 g of methanol was produced. The water concentration in methanol after the experiment was 3.6 wt %.

(6c) Methanol Solution of 9 wt % Water

Example 6a was repeated at 141 bar and 200° C. re-using the same catalyst as used in Examples 6a and 6b. Water was added to an initial concentration of 9 wt % in methanol. The pressure drop was in total 47.8 bar and 7.8 g of methanol was produced. The water concentration after the experiment was 7.6 wt %.

TABLE 3

Methanol production in presence of water for gas B

| P (bar) | T (° C.) | [H$_2$O] wt % | ΔP (bar) | MeOH (g) |
|---|---|---|---|---|
| 138 | 200 | <0.05 | 55.6 | 9.1 |
| 139 | 200 | 5 | 48.3 | 7.9 |
| 141 | 200 | 9 | 47.8 | 7.8 |

Example 7

Reduction of Methyl Formate Concentration.

This example illustrates that the concentration of the abundant by-product methyl formate can be reduced significantly by chemical equilibrium between hydrogen, carbon monoxide, methyl formate and methanol in reaction (7) and (8). Hence, if a methyl-formate-rich stream is recycled to the reactor, there will be no net production of methyl formate in the reactor.

The experiment was run with an initial concentration of 34.8 mole % methyl formate in a methanol suspension. The experiment was carried out at 200° C. and 132 bar using the same procedure as in the examples above. At 132 bar and 200° C., reactions (1) and (2) are shifted towards methanol production. Fresh, activated catalyst was employed. The hydrogen-rich synthesis gas B was used. The pressure drop in the reservoir was 29 bar. The final concentration of methyl formate was reduced to 5.4 mole % in the liquid phase. This corresponds to an analysed exit dry gas concentration of hydrogen of around 24 mole %.

TABLE 4

Liquid concentration of MF and methanol before and after experiment

| Component | $X_L$ [mole %] start | $X_L$ [mole %] end |
|---|---|---|
| Methyl formate | 34.8 | 5.4 |
| Methanol | 65.2 | 94.6 |

We claim:

1. A process for preparing methanol from a synthesis gas comprising carbon monoxide, carbon dioxide and hydrogen by steps of:
   (a) passing the synthesis gas into a reactor containing a solid methanol conversion catalyst particles being suspended in a liquid phase of methanol and water;
   (b) reacting the synthesis gas in presence of the suspended catalyst at a pressure and temperature, where methanol being formed on the catalyst condenses into the liquid phase;
   (c) withdrawing from the reactor a part of the liquid phase containing formed methanol product; and
   (d) recycling a stream comprising methanol and at least one of the compounds of methyl formate and ethanol into the liquid phase obtained in step (b) to establish chemical equilibrium and to suppress formation of the at least one of the compounds.

2. A process in accordance with claim 1, wherein the amount of water being present in the liquid phase is 0–10 wt %.

3. A process in accordance with claim 1, wherein the pressure in the slurry bed reactor is 50–290 bar.

4. A process in accordance with claim 1, wherein the temperature in the slurry bed reactor is between 150° C. to 240° C.

5. A process in accordance with claim 1, wherein the synthesis gas has a $CO_2/CO$ molar ratio of 0.02–1.0 and an $H_2/CO$ molar ratio of 2–4.

6. A process in accordance with claim 1, wherein the synthesis gas comprises 15–35 vol. % CO, 60–74 vol. % $H_2$ and 0–15 vol. % $CO_2$.

7. A process of claim 1 further comprising of a step of recycling an effluent gas stream being withdrawn from the reactor.

8. A process of claim 1, wherein the reacting synthesis gas is cooled by internal cooling means.

9. A process of claim 1, wherein methanol and/or catalyst is added as fresh or being recycled to the reactor.

10. A process in accordance with claim 1, wherein the amount of water being present in the liquid phase is 0–3 wt %.

11. A process in accordance with claim 1, wherein the pressure in the slurry bed reactor is 60–140 bar.

12. A process in accordance with claim 1, wherein the pressure in the slurry bed reactor is 180–225° C.

* * * * *